(12) United States Patent
Mogatadakala

(10) Patent No.: US 10,720,236 B2
(45) Date of Patent: Jul. 21, 2020

(54) SYSTEM AND METHOD FOR PREDICTIVE MAINTENANCE OF MEDICAL DIAGNOSTIC MACHINE COMPONENTS

(71) Applicant: DI Insights, LLC, Schaumburg, IL (US)

(72) Inventor: Venkata Kishore Mogatadakala, Schaumburg, IL (US)

(73) Assignee: DI Insights, LLC, Schaumburg, IL (US)

( * ) Notice: Subject to any disclaimer, the term of this patent is extended or adjusted under 35 U.S.C. 154(b) by 149 days.

(21) Appl. No.: 15/942,424

(22) Filed: Mar. 30, 2018

(65) Prior Publication Data

US 2019/0304600 A1 Oct. 3, 2019

(51) Int. Cl.
*G16H 40/40* (2018.01)
*A61B 6/00* (2006.01)
*G16H 40/20* (2018.01)

(52) U.S. Cl.
CPC ............. *G16H 40/40* (2018.01); *A61B 6/586* (2013.01); *A61B 6/581* (2013.01); *G16H 40/20* (2018.01)

(58) Field of Classification Search
CPC . G06T 7/0012; G06F 19/321; G05B 23/0294; G16H 50/20; G16H 40/40; G06Q 50/22; G06K 9/6265; A61B 6/586
See application file for complete search history.

(56) References Cited

U.S. PATENT DOCUMENTS

| | | | | |
|---|---|---|---|---|
| 4,991,193 | A * | 2/1991 | Cecil | A61B 6/10 378/117 |
| 2016/0209837 | A1* | 7/2016 | Kim | G05B 23/0275 |
| 2019/0057767 | A1* | 2/2019 | Wilson | G16H 40/20 |

* cited by examiner

*Primary Examiner* — Yara B Green
(74) *Attorney, Agent, or Firm* — Incubate IP; Randy R. Micheletti

(57) ABSTRACT

The present disclosure provides components, systems, and methods for predictive maintenance of medical diagnostic machine components.

19 Claims, 9 Drawing Sheets

SYSTEM AND METHOD FOR PREDICTIVE MAINTENANCE OF MEDICAL DIAGNOSTIC MACHINE COMPONENTS

TECHNICAL FIELD

The present disclosure generally relates to the field of medical diagnostic machine. More particularly, the present disclosure relates to a system and method for predictive maintenance of medical diagnostic machine components.

BACKGROUND

Physiological activity of various organs, such as the heart or brain, may be monitored, and this physiological activity may be analysed to look for patterns that may assist in diagnosing various conditions. Typically, the medical diagnostic machine monitors the physiological activity of various organs. The medical diagnostic machine includes, but is not limited to, magnetic resonance imaging machine, computed tomography machine, X-ray machine, nuclear medicine machine, and the like.

In medical environments, users often demand high availability of medical diagnostic machines. However, the medical diagnostic machine components may require periodic maintenance, such as repair or replacement. Indeed, the performance of the medical diagnostic machine components may degrade due to wear, thereby reducing its efficiency.

Being able to predict the current health condition of some key components in the medical diagnostic machine saves good amount of money in servicing the machines. This will enable proactive service and maintenance of the medical diagnostic machine before the key components breakdown. If components break, it not only costs lot of money to replace them but also causes the system to shut down, which will result in lost revenue for a healthcare facility environment. The healthcare facility environment includes, but is not limited to, hospitals, healthcare providers, clinics, diagnostic centres, and the like. Currently, the available solutions have remote monitoring capabilities i.e., monitor the components information remotely, setup triggers and alerts and respond to critical conditions. But, the available solutions don't help in knowing when a next problem can occur and also can't do predictions. Non-availability of the predictive models, demands scheduled trips to be made by the technicians to the healthcare facility environment to evaluate conditions of the components. As a consequence, the information can't be utilized remotely and increases the unnecessary preventive maintenance trips to the healthcare facility environment.

In the light of aforementioned discussion there exists a need for certain system with novel methodologies that would overcome or ameliorate the above-mentioned disadvantages.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

An objective of the present disclosure is directed towards predicting the health condition of certain medical diagnostic machine components to save time and money in servicing the medical diagnostic machines.

Another objective of the present disclosure directed towards reporting the predicted times to replace certain medical diagnostic machine components to an end-user device in real time.

According to an embodiment of the present disclosure, a system comprises a sensing information acquisition unit comprises at least one processing device, a processing device electrically coupled to a plurality of sensors and the plurality of sensors configured to detect functioning of medical diagnostic machine components.

According to another embodiment of the present disclosure, the system further comprises at least one end-user device configured to receive digital sensing data from at least one processing device and the at least one end-user device also configured to receive quality control (QA) data in digital imaging and communications in medicine (DICOM) format from the medical diagnostic machine components, the one end-user device comprises a data analytics platform configured to collect the sensing data and QA-DICOM data, the data analytics platform configured to determine the health of the medical diagnostic machine components and predict time to replace the medical diagnostic machine components by the collected digital sensing data and QA-DICOM data using specific matrix variables.

BRIEF DESCRIPTION OF DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein.

DETAILED DESCRIPTION

Figure 1:
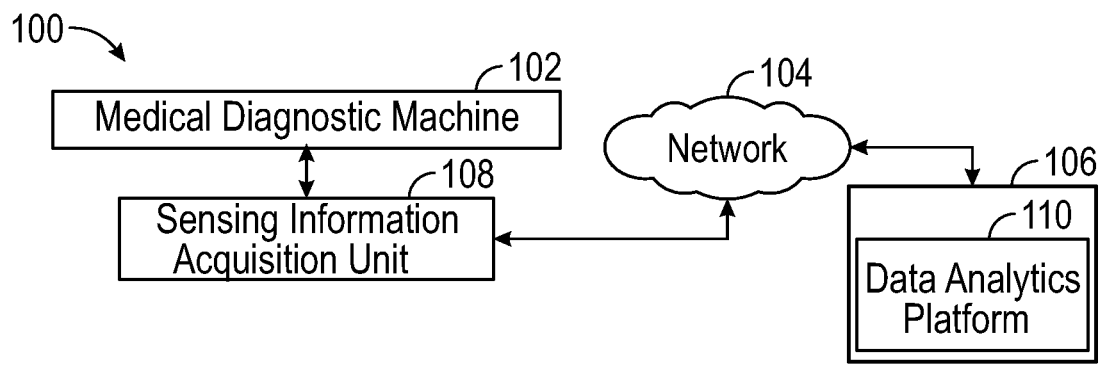
FIG. 1 is a block diagram depicting an environment for predictive maintenance of medical diagnostic machine, in accordance with one or more embodiments.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

Referring to FIG. 1, FIG. 1 is a block diagram 100 depicting an environment for predictive maintenance of medical diagnostic machine components, in accordance with one or more embodiments. The environment 100 depicts a medical diagnostic machine 102, a network 104, an end-user device 106, and a sensing information acquisition unit 108. The medical diagnostic machine 102 may also be referred as medical diagnostic imaging machine. The medical diagnostic machine 102 includes components which may not be limited to, radio frequency body coil, gradient coil, inner vacuum vessel, inner thermal shield, inner helium vessel, outer helium vessel, outer thermal shield, outer vacuum vessel, X-ray tube, and detectors. The medical diagnostic machine 102 may further include sensors (not shown) configured to detect the functioning of each component in the medical diagnostic machine 102. The end-user device 106 may include a device such as a personal computer or desktop, a workstation, an electronic book reader, a personal digital assistant, a mobile station, mobile phones, computing tablets, and the like. The sensing information acquisition unit 108 may be an embedded computer with real time operating system and capacitive touch screen user interface. The sensing information acquisition unit 108 may be configured to acquire sensing data from the sensors (not shown). The end-user device 106 may be configured to collect DICOM (Digital Imaging and Communications in Medicine) data from the medical diagnostic machine 102 through the network 104. The network 104 may include but is not limited to, an Internet of things (IoT network devices), an Ethernet, a wireless local area network (WLAN), or a wide area network (WAN), a Bluetooth low energy network, a ZigBee network, a WIFI communication network e.g., the wireless high speed internet, or a combination of networks, a cellular service such as a 4G (e.g., LTE, mobile WiMAX) or 5G cellular data service, a RFID module, a NFC module, wired cables, such as the world-wide-web based Internet, or other types of networks may include Transport Control Protocol/Internet Protocol (TCP/IP) or device addresses (e.g. network-based MAC addresses, or those provided in a proprietary networking protocol, such as Modbus TCP, or by using appropriate data feeds to obtain data from various web services, including retrieving XML data from an HTTP address, then traversing the XML for a particular node) and the like without limiting the scope of the present disclosure.

The end-user device 106 may include a data analytics platform 110. The data analytics platform 110 may be accessed as a mobile application, a web application or other software application known in the art of further implemented, without limiting the scope of the present disclosure. The data analytics platform 110 may be configured to collect the digital sensing data and DICOM image data from the end-user device 106. The data analytics platform 110 may include linear classifier based algorithms. The data analytics platform 110 may compare variables in tables with predefined thresholds using symbols and transmit alerts to the end-user device 106. In some embodiments, the transmitted alert enables the end-user to access analysis results associated with analytical results produced by the data analytics platform 110. For example, the end-user device 106 may enable the end-user to access the analysis results using API calls in some embodiments. The data analytics platform 110 may be configured to predict the health of the components and also predict the time to replace components.

The data analytics platform 110 may include a linear classifier matrix M, Training and determining linear classifier matrix M:

$$Y_{known} = M_{unknown} X_{known}$$

wherein:

$Y_{known}$ and $X_{known}$ are known data matrix derived from historical data or analytical equations;

$X_{known}$ is referred as a first matrix set, $Y_{known}$ is referred as a second matrix set, and $M_{unknown}$ is referred as a third matrix set.

Unstable solutions may result in for the third matrix set M unknown while inverting the first matrix set $X_{known}$ if $X_{known}$ is ill conditioned. The ill-condition ness often occurs if some columns in the first matrix set $X_{known}$ contain significant correlation between each other. To obtain stable results a singular value decomposition based model is used for inverting the first matrix set $X_{known}$.

Third matrix set M unknown is determined using regularized singular value decomposition technique:

1. The first matrix set $X_{known}$ is decomposed into eigen vector matrices U and V; Eigen value matrix W as shown below $$X_{known} = UWV^T$$

2. Smaller diagonal values in $W^{-1}$ are set to zero
3. The third matrix set $M_{unknown}$ is estimated as follows:

$$M_{unknown} = Y_{known} VW^{-1} U^T$$

U is a matrix whose columns are the eigenvectors of $X_{known} X^T_{known}$ (AKA left eigenvectors)

W is a diagonal matrix whose diagonal elements are the singular values of $X_{known}$ V is a matrix whose columns are the eigenvectors of known $X^T_{known} X_{known}$ (AKA right eigenvectors)

Figure 2:
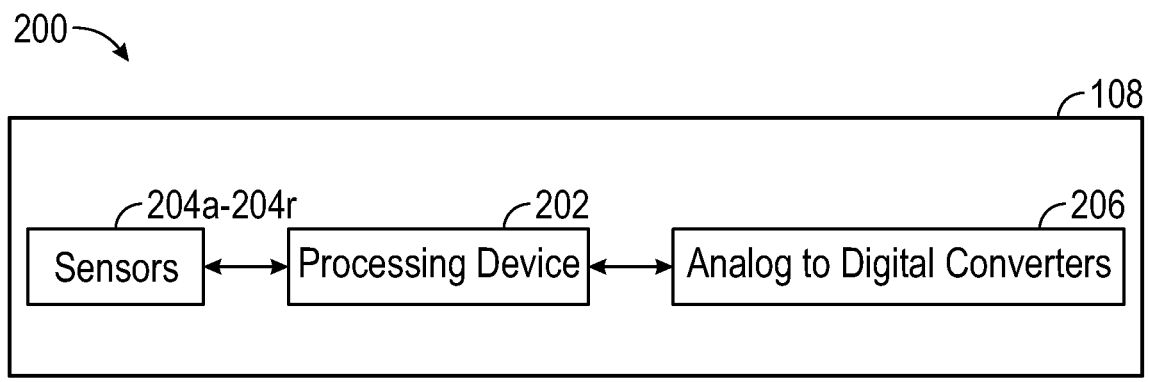
FIG. 2 is a diagram depicting the sensing information acquisition unit 108 shown in FIG. 1, in accordance with one more embodiments.

Referring to FIG. 2, FIG. 2 is a diagram 200 depicting the sensing information acquisition unit 108 shown in FIG. 1, in accordance with one more embodiments. The sensing information acquisition unit 108 may be inbuilt in the end-user device 106 or add-on to the end-user device 106. The sensing information acquisition unit 108 may include a processing device 202. The processing device 202 includes, but is not limited to, a microcontroller (for example ARM 7 or ARM 11), a microprocessor, a digital signal processor, a microcomputer, a field programmable gate array, a programmable logic device, a state machine or a logic circuitry. The sensing information acquisition unit 108 may further include sensors 204a-204r which are electrically coupled to the processing device 202. The sensors 204a-204r may be configured to detect the functioning of medical diagnostic machine components and process the detected data by the processing device 202.

The sensing information acquisition unit 108 may further include analog to digital converters 206 which are electrically coupled to the processing device 202. The analog to digital converters 206 may be configured to convert the detected analog sensing data into digital sensing data. The term "analog sensing data" may refer to analog values received from the sensors 204a-204r that measure values from the medical diagnostic machine components, a digital value converted or a data wave modulated in the processing device 202. The processing device 202 may be configured to transmit the digital sensing data to the end-user device 106 through the network 104. The data analytics platform 110 may be configured to collect the digital sensing data from the end-user device 106 via the network 104.

Figure 3:
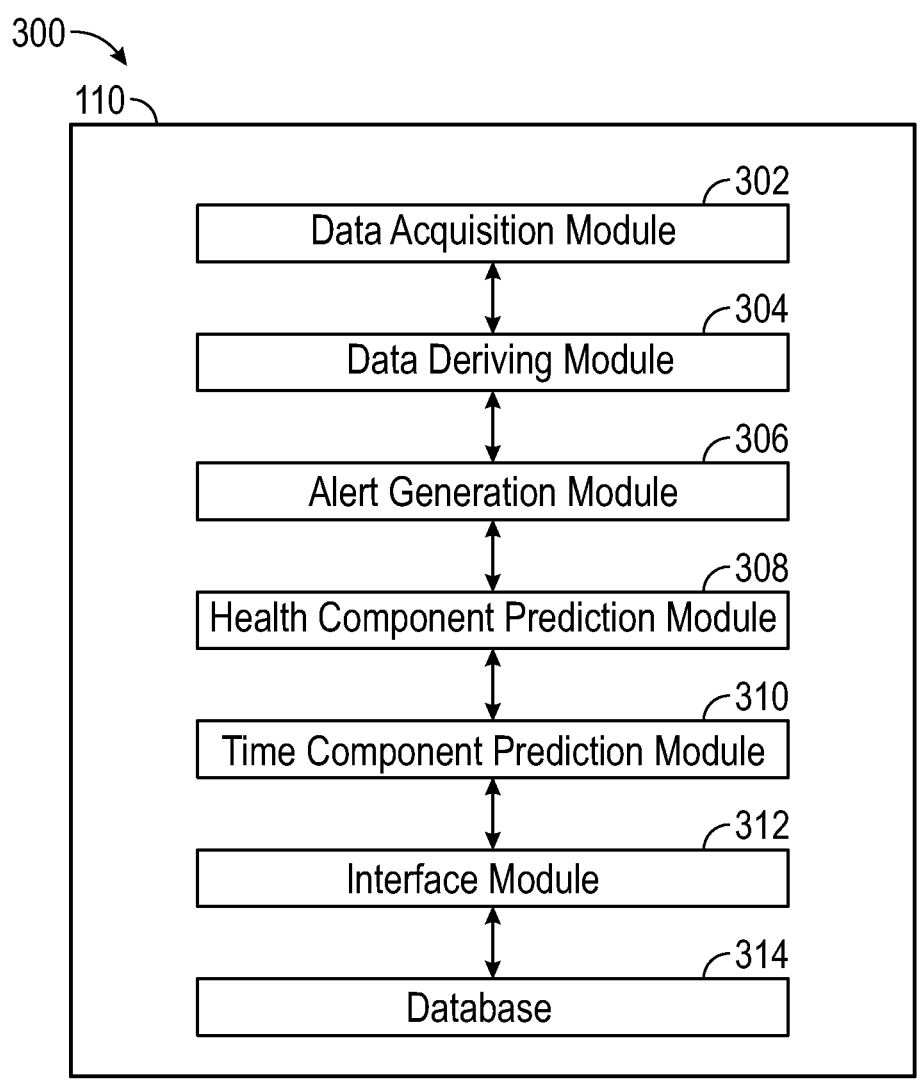
FIG. 3 is a diagram depicting the data analytics platform 110 shown in FIG. 1, in accordance with one or more embodiments.

Referring to FIG. 3, FIG. 3 is a diagram 300 depicting the data analytics platform 110 shown in FIG. 1, in accordance with one or more embodiments. The data analytics platform 302 may further include a data acquisition module 302, a data deriving module 304, an alert generation module 306, a health component prediction module 308, a time component prediction module 310, an interface module 312, and a database 314. The data acquisition module 302 may be configured to acquire the digital sensing data and QA-DICOM data from the end-user device 106. The data may be received using an application programming interface (e.g., HTTP or HTTPS POST API) and the received data may be saved in the database 314. The database 314 may include the raw data or noise filtered raw digital sensing data and QA-DICOM data. The data deriving module 304 may be configured to derive the digital sensing data and QA-DICOM data from the database 314. The alert generation module 306 may be configured to generate alerts and transmit to the end-user device 106 when the collected sensing data and QA-DICOM data varied with predefined thresholds. Here, the predefined threshold may include, but is not limited to, historical data, training data and the like. The digital sensing data and QA-DICOM data may be compared with the predefined thresholds using symbols (e.g. $>, <, ==, <=, >=$). The alerts may include, but are not limited to, text messages, notifications, emails, pop-up notifications, multimedia messaging service, voice mail or facsimile, and the like. The health component prediction module 308 may be configured to predict the health of the medical diagnostic machine components based on the derived data and the specific matrix variables. The time component prediction module 310 may be configured to predict the time to replace the medical diagnostic machine components based on predicted health of the medical diagnostic machine components. The interface module 312 may be configured to allow users to access variables or charts from the database 314 through the HTTP/HTTPS GET API requests.

Figure 4A:
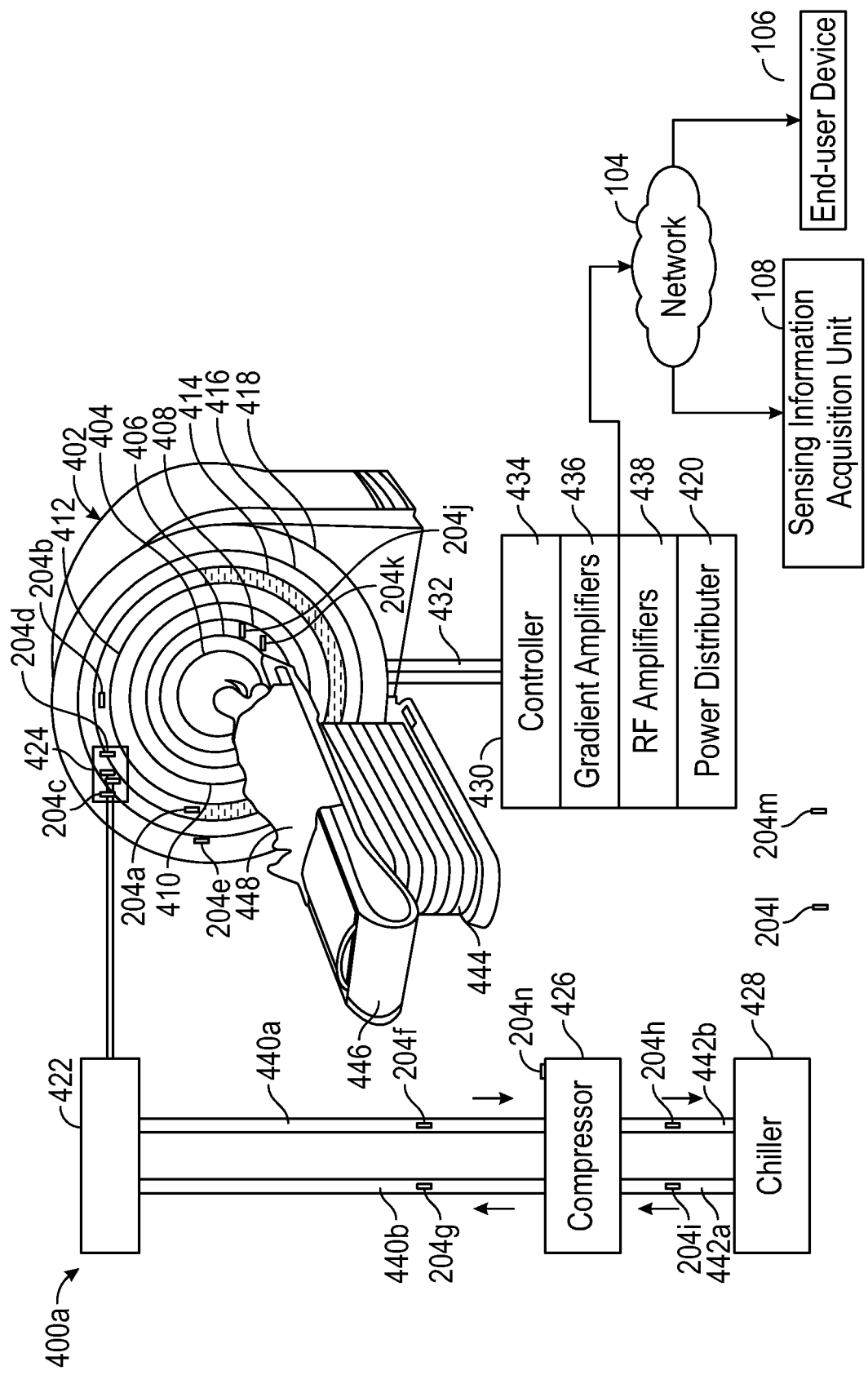
FIG. 4A is an example diagram depicting the magnetic resonance imaging (MRI) machine scanner room, in accordance with one or more embodiments.

Referring to FIG. 4A, FIG. 4A is an example diagram 400a depicting the magnetic resonance imaging (MRI) machine scanner room, in accordance with one or more embodiments. The example diagram 400a depicts the magnetic resonance imaging machine 402 (herein after referred as MRI machine) connected to the sensing information acquisition unit 108 and the end-user device 106. The MRI machine 402 may include components which may include a RF body coil 404, a gradient coil 406, an inner vacuum vessel 408, an inner thermal shield 410, an inner helium vessel 412, an outer helium vessel 414, an outer thermal shield 416, an outer vacuum vessel 418, a cold head 422, a re-condenser 424, a compressor 426, and a chiller 428. The example diagram 400a further depicts a system cabinet 430 which is electrically coupled to the MRI machine 402 through cables 432. The system cabinet 430 may include a controller 434, gradient amplifiers 436, and radio frequency (RF) amplifiers 438. The controller 434 may be programmed with operational protocols which is configured to control the pulse sequences, and the like. The gradient amplifier 436 may be configured for driving the gradient coil. The RF amplifiers 438 may be configured to produce radio frequency signals which are used to knock down spins within the MRI machine 402. The system cabinet 430 may be configured for data acquisition, and an image reconstruction. The system cabinet 430 may be configured to establish communication with the sensing information acquisition unit 108 and the end-user device 106 through the network 104. The system cabinet 430 may further include a power distributor 420. The power distributor 420 may be configured for distributing the power to the medical diagnostic machine components.

The recondenser 424 may be attached to the cold head 422. The example diagram 400a may further depict flex lines 440a-440b. The flex lines 440a-440b may be configured to supply helium gas to the cold head 422 from the compressor 426, and also return the helium gas to the compressor 426 from the cold head 422. The chiller 428 may have tubes 442a-442b which may be configured to provide low temperature and high temperature to the compressor 426. The example diagram 400a further depicts sensors 204a-204n positioned at different portions of the medical diagnostic machine components. The sensors 204a-204n include, but are not limited to, helium sensor, helium gas pressure sensor, cold head temperature sensor, re-condenser temperature sensor, thermal shield temperature sensor, helium gas low pressure sensor, helium gas high pressure sensor, water low temperature sensor, water high temperature sensor, acoustic sensor (e.g., MRI noise acoustic sensor), vibration sensor (e.g., MRI vibration sensor), room humidity sensor, room temperature sensor, and compressor pressure sensor. The example diagram 400a further depicts a support table 444 and a carrier 446. The carrier 446 along with a patient 448 may be positioned on the support table 444. After the carrier 446 is positioned on the support table 444 and moved into engagement with the RF body coil 404.

The helium sensor 204a may be positioned between the inner helium vessel 412 and the outer helium vessel 414. The helium sensor 204a may be configured to detect the liquid helium level between the inner helium vessel 412 and the outer helium vessel 414. The helium gas pressure sensor 204b may also be positioned between the inner helium vessel 412 and the outer helium vessel 414. The helium gas pressure sensor 204b may be configured for measuring the pressure of helium gas between the inner helium vessel 412 and the outer helium vessel 414. The cold head temperature sensor 204c may be positioned at the cold head 422. The cold head temperature sensor 204c may be configured to sense the temperature of the cold head 422 and generate a temperature signal. The re-condenser temperature sensor 204d may be positioned on the re-condenser 424. The re-condenser temperature sensor 204d may be configured to sense the variations in the temperature at the re-condenser 424. The thermal shield temperature sensor 204e may be positioned on the outer thermal shield 416. The thermal shield temperature sensor 204e may be configured to sense the temperature around the outer thermal shield 416. The helium gas low pressure sensor 204f and the helium gas high pressure sensor 204g may be positioned on the flex lines 440a-440b. The helium gas low pressure sensor 204f may be configured to determine the low pressure of the helium gas at the flex line 440a. The helium gas high pressure sensor 204g may be configured to determine the high pressure of the helium gas at the flex line 440b. The water high temperature sensor 204h may be positioned on the tube 442b and the water high temperature sensor 204h may be configured to determine the high temperatures of the water in the tube 442b. The water low temperature sensor 204i may be positioned on the tube 442a and the water low temperature sensor 204i may be configured to determine the low temperatures of the water in the tube 442a. The acoustic sensor 204j may be positioned between the gradient coil 406 and the inner vacuum vessel 408. The acoustic sensor 204j may be configured for sensing an acoustic signal originating from the gradient coil 406 and the inner vacuum vessel 408. The vibration sensor 204k may be positioned between the gradient coil 406 and the inner vacuum vessel 408. The vibration sensor 204k may be configured to measure the vibration response of the gradient coil 406 and the inner vacuum vessel 408. The vibration sensor 204k may include a motion sensor to measure relative motion between the gradient coil 406 and the inner vacuum vessel and transmit signals related to the sensed motion. The room temperature sensor 204l and the humidity sensor 204m may be positioned in the magnetic resonance imaging machine scanner room 400. The room temperature sensor 204l may be configured to measure the actual room temperature in a space (where the (MRI) machine 402 is positioned) and generate a temperature signal indicative thereof. The humidity sensor 204m may be configured to measure the actual room humidity in space and generate a humidity signal indicative thereof. The pressure sensor 204n may be positioned on the compressor 426 and the pressure sensor 204n may be configured to provide pressure readings from selected points within the compressor 426.

Figure 4B:
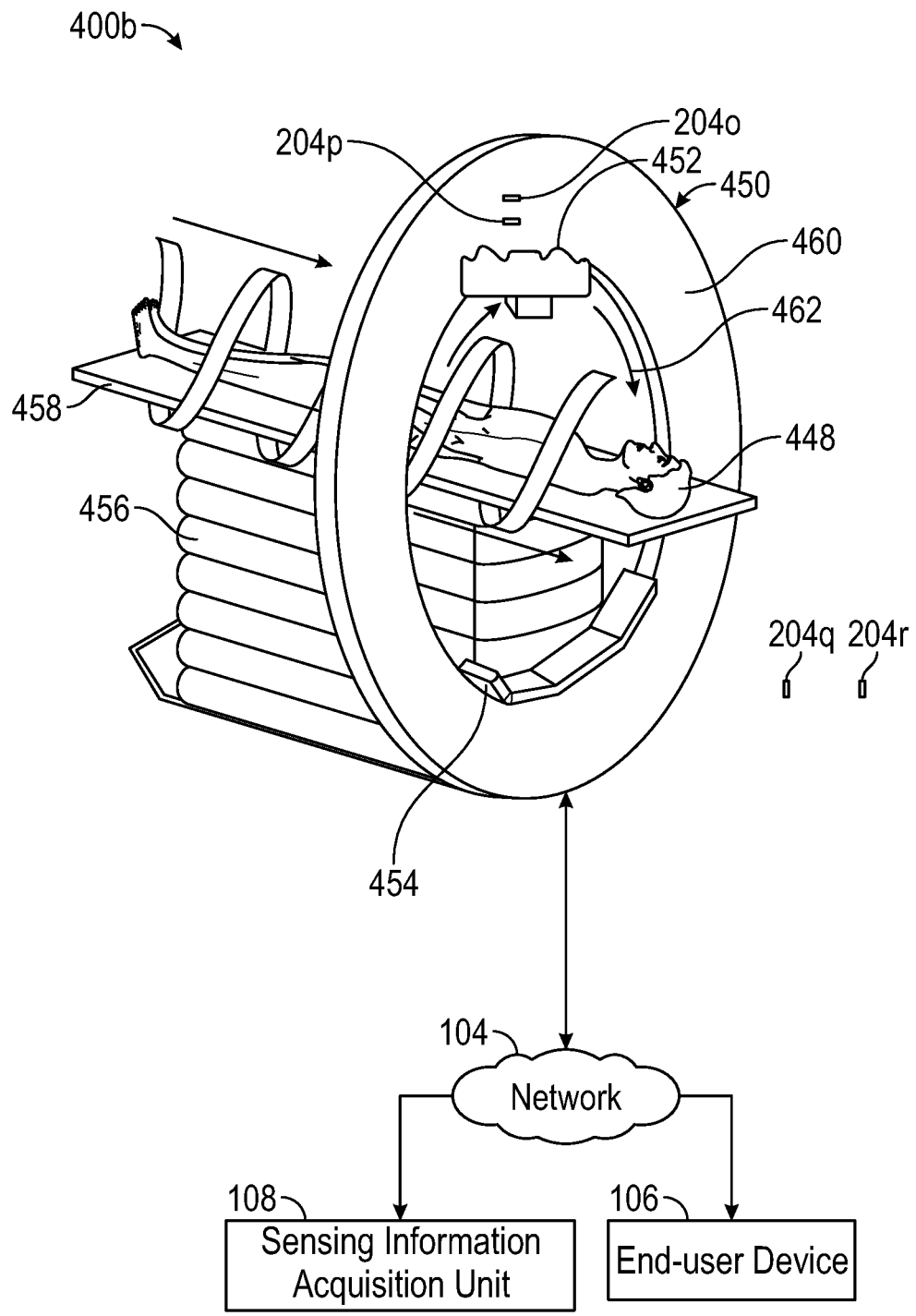
FIG. 4B is an example diagram depicting the computed tomography scanner room, in accordance with one or more embodiments.

Referring to FIG. 4B, FIG. 4B is an example diagram 400b depicting the computed tomography scanner room, in accordance with one or more embodiments. The example diagram 400b depicts the computed tomography machine 450 (herein after referred as CT machine) connected to the sensing information acquisition unit 108 and the end-user device 106. The CT machine 450 may include components which may include, an X-ray tube 452, an array of detectors 454, a support table 456, a carrier 458, and a translating plate 460. The CT machine 450 may be configured to establish communication with the sensing information acquisition unit 108 and the end-user device 106 through the network 104. The carrier 458 along with the patient 448 may be positioned on the support table 456. Once the carrier 458 is positioned on the support table 456, it is moved into engagement with the translating plate 460. The X-ray tube 452 may be rigidly coupled to the translating plate 460 by any fastening means opposite from the array of detectors 454. The fastening means may include, but are not limited to screws, clamps, straps, and the like. The array of detectors 454 may be mechanically coupled together by any fastening means. The X-ray tube 452 may be configured to generate an X-ray beam 462. The array of detectors 454 may be configured to be capable of detecting X-ray photons of the X-ray beam 462. The example diagram 400b further depicts sensors 204o-204r which may include, acoustic sensor, the vibration sensor, the room temperature sensor, and the humidity sensor. The acoustic sensor 204o and the vibration sensor 204p may be positioned on the translating plate 460. The acoustic sensor 204o may be configured for sensing an acoustic signal originating from the translating plate 460. The vibration sensor 204p may be configured to measure the vibration response of the translating plate 460. The room temperature sensor 204q and the humidity sensor 204r may be positioned in the computed tomography machine scanner room 400b. The room temperature sensor 204q may be configured to measure the actual room temperature in space (where the CT machine 450 positioned) and generate a temperature signal indicative thereof. The humidity sensor 204r may measure the actual room humidity in a space and generate a humidity signal indicative thereof.

The data analytics platform 110 may be configured to collect the digital sensing data and QA-DICOM data from the end-user device 106. The below tables depict the digital sensing data description and QA-DICOM data description,

| Sensor | Description | Raw or filtered raw data variable name |
|---|---|---|
| S1 | Helium level | $x_1^{raw}$ |
| S2 | Helium gas pressure | $x_2^{raw}$ |
| S3 | Cold head Temperature | $x_3^{raw}$ |
| S4 | Re-condenser Temperature | $x_4^{raw}$ |
| S5 | Thermal shield temperature | $x_5^{raw}$ |
| S6 | Helium gas low pressure | $x_6^{raw}$ |
| S7 | Helium gas high pressure | $x_7^{raw}$ |
| S8 | Water low temperature | $x_8^{raw}$ |
| S9 | Water high temperature | $x_9^{raw}$ |
| S10 | MRI acoustic noise | $x_{10}^{raw}$ |
| S11 | MRI vibration | $x_{11}^{raw}$ |
| S12 | MRI machine room temperature | $x_{12}^{raw}$ |
| S13 | MRI machine room humidity | $x_{13}^{raw}$ |
| S14 | X-Ray tube acoustic noise | $x_{14}^{raw}$ |
| S15 | X-Ray tube vibration | $x_{15}^{raw}$ |
| S16 | CT system room temperature | $x_{16}^{raw}$ |
| S17 | CT system room humidity | $x_{17}^{raw}$ |
| S18 | Compressor pressure | $x_{18}^{raw}$ |

| Raw or filtered raw data variable name | Description | Calculated from DICOM data |
|---|---|---|
| $x_{B0}^{raw}$ | Magnet center frequency | MRI "qa" or "acr" images |
| $x_{tx}^{raw}$ | Transmit gain | MRI "qa" or "acr" images |
| $x_{rx}^{raw}$ | Receive gain | MRI "qa" or "acr" images |
| $x_{SNR}^{raw}$ | Signal to noise ratio | MRI "qa" or "acr" images |
| $x_{gx}^{raw}$ | Geometric accuracy in - X direction | MRI "qa" or "acr" images |
| $x_{gy}^{raw}$ | Geometric accuracy in - Y direction | MRI "qa" or "acr" images |
| $x_{gz}^{raw}$ | Geometric accuracy in - Z direction | MRI "qa" or "acr" images |
| $x_M^{raw}$ | Magnitude stability | MRI "qa" or "acr" images with at-least 2 echoes |
| $x_P^{raw}$ | Phase stability | MRI "qa" or "acr" images with at-least 2 echoes |
| $x_{kV}^{raw}$ | kV | Any CT image |
| $x_{mAs}^{raw}$ | mAs | Any CT image |
| $x_{CTW}^{raw}$ | Water CT Number | CT "qa" or "acr" images |
| $x_{CTA}^{raw}$ | Air CT Number | CT "qa" or "acr" images |

The below tables depict the derived data variables from the digital sensing data and QA-DICOM data in the database 314,

| Derived data variable name | Derived variable description |
|---|---|
| $x_1^d$ | $\dfrac{d[x_1^{raw}]}{dt}$ |
| $x_2^d$ | $\text{duty\_cycle}(x_2^{raw})$ |
| $x_{22}^d$ | $\dfrac{d[x_2^d]}{dt}$ |
| $x_3^d$ | $\dfrac{d[x_3^{raw}]}{dt}$ |
| $x_4^d$ | $d[abs(x_4^{raw}) - abs(x_5^{raw})]$ |

-continued

| Derived data variable name | Derived variable description |
|---|---|
| $x_5^d$ | $\dfrac{d[\text{abs}(x_4^{raw}) - \text{abs}(x_5^{raw})]}{dt}$ |
| $x_6^d$ | $d[\text{abs}(x_6^{raw}) - \text{abs}(x_7^{raw})]$ |
| $x_7^d$ | $\dfrac{d[\text{abs}(x_6^{raw}) - \text{abs}(x_7^{raw})]}{dt}$ |
| $x_8^d$ | $d[\text{abs}(x_8^{raw}) - \text{abs}(x_9^{raw})]$ |
| $x_9^d$ | $\dfrac{d[\text{abs}(x_8^{raw}) - \text{abs}(x_9^{raw})]}{dt}$ |
| $x_{10}^d$ | $\dfrac{d[x_{18}^{raw}]}{dt}$ |
| $x_{B0}^d$ | $x_{B0}^d = \dfrac{d[x_{B0}^{raw}]}{dt}$ |
| $x_{TX}^d$ | $x_{TX}^d = \dfrac{d[x_{TX}^{raw}]}{dt}$ |
| $x_{RX}^d$ | $x_{RX}^d = \dfrac{d[x_{RX}^{raw}]}{dt}$ |
| $x_{SNR}^d$ | $x_{SNR}^d = \dfrac{d[x_{SNR}^{raw}]}{dt}$ |
| $x_{GX}^d$ | $x_{GX}^d = \dfrac{d[x_{GX}^{raw}]}{dt}$ |
| $x_{GY}^d$ | $x_{GY}^d = \dfrac{d[x_{GY}^{raw}]}{dt}$ |
| $x_{GZ}^d$ | $x_{GZ}^d = \dfrac{d[x_{GZ}^{raw}]}{dt}$ |
| $x_M^d$ | $x_M^d = \dfrac{d[x_M^{raw}]}{dt}$ |
| $x_P^d$ | $x_P^d = \dfrac{d[x_P^{raw}]}{dt}$ |
| $x_{kV}^d$ | $x_{kV}^d = \displaystyle\int x_{kV}^{raw}$ |
| $x_{mAs}^d$ | $x_{mAs}^d = \displaystyle\int x_{mAs}^{raw}$ |
| $x_{CTW}^d$ | $x_{CTW}^d = \dfrac{d[x_{CTW}^{raw}]}{dt}$ |
| $x_{CTA}^d$ | $x_{CTW}^d = \dfrac{d[x_{CTA}^{raw}]}{dt}$ |

The data analytics platform 110 may be configured to collect the QA-DICOM data and the digital sensing data from the end-user device 106. The data analytics platform 110 may be configured to predict the health of the components in the medical diagnostic machine 102 based on the collected QA-DICOM data and digital sensing data. The data analytics platform 110 may be configured to predict the current health of the cold head component 422. The data analytics platform 110 includes, Matrix $X_{CH}$ is projected onto matrix $M_{CH}$, which is derived from training data as described in the linear classifier matrix M $Y_{CH}$ is calculated health for cold head is classified as "OK" or "WARNING" or "CRITICAL" depending on which ever element is higher in matrix $Y_{CH}$ $X_{CH} = [x_1^d \ x_2^d \ x_{22}^d \ x_3^d \ x_4^d \ x_5^d \ x_6^d \ x_7^d \ x_8^d \ x_9^d \ X_{10}^d]^T$ $Y_{CH} = M_{CH} X_{CH}$ $Y_{CH} = [Y_{CH}^{OK} \ Y_{CH}^{WARNING} \ Y_{CH}^{CRITICAL}]^T$ $X_{CH}$ = Coldhead input parameter matrix: 11×1
$M_{CH}$ = Coldhead Linear classifier matrix: 3×11
$Y_{CH}$ = Coldhead health matrix: 3×1

The data analytics platform 110 may be configured to predict the current health of the magnet field homogeneity. The data analytics platform 110 includes, Matrix $X_{FIELD}$ is projected onto matrix $M_{FIELD}$, which is derived from training data as described in the linear classifier matrix M $Y_{FIELD}$ is calculated health for cold head is classified as "OK" or "WARNING" or "CRITICAL" depending on which ever element is higher in matrix $Y_{FIELD}$ $X_{FIELD} = [x_{B0}^{raw} \ x_{B0}^d \ x_{SNR}^{raw} \ x_{SNR}^d \ x_{GX}^{raw} \ x_{GX}^d \ x_{GY}^{raw} \ x_{GY}^d \ x_{GZ}^{raw} \ x_{GZ}^d]^T$ $Y_{FIELD} = M_{FIELD} X_{FIELD}$ $Y_{FIELD} = [Y_{FIELD}^{OK} \ Y_{FIELD}^{WARNING} \ Y_{FIELD}^{CRITICAL}]^T$ $X_{FIELD}$ = Coldhead input parameter matrix: 10×1
$M_{FIELD}$ = Coldhead Linear classifier matrix: 3×10
$Y_{FIELD}$ = Coldhead health matrix: 3×1

The data analytics platform 110 may be configured to predict the current health of the MRI overall image quality. The data analytics platform 110 includes, Matrix $X_{MRI\_IQ}$ is projected onto matrix $M_{MRI\_IQ}$, which is derived from training data as described in the linear classifier matrix M $Y_{MRI\_IQ}$ is calculated health for cold head is classified as "OK" or "WARNING" or "CRITICAL" depending on which ever element is higher in matrix $Y_{MRI\_IQ}$ $X_{MRI\_IQ} = [x_{SNR}^{raw} \ x_{SNR}^d \ x_{GX}^{raw} \ x_{GX}^d \ x_{GY}^{raw} \ x_{GY}^d \ x_{GZ}^{raw} \ x_{GZ}^d \ x_M^{raw} \ x_M^d \ x_P^{raw} \ x_P^d]^T$ $Y_{MRI\_IQ} = M_{MRI\_IQ} X_{MRI\_IQ}$ $Y_{MRI\_IQ} = [Y_{MRI\_IQ}^{OK} \ Y_{MRI\_IQ}^{WARNING} \ Y_{MRI\_IQ}^{CRITICAL}]^T$ $X_{MRI\_IQ}$ = MRI IQ input parameter matrix: 12×1
$M_{MRI\_IQ}$ = MRI IQ Linear classifier matrix: 3×12
$Y_{MRI\_IQ}$ = MRI IQ health matrix: 3×1

The data analytics platform 110 may be configured to predict the current health of the CT tube. The data analytics platform 110 includes, Matrix $X_{TUBE}$ is projected onto matrix $M_{TUBE}$, which is derived from training data as described in the linear classifier matrix M $Y_{TUBE}$ is calculated health for cold head is classified as "OK" or "WARNING" or "CRITICAL" depending on which ever element is higher in matrix $Y_{TUBE}$ $X_{TUBE} = [x_{14}^{raw} \ x_{15}^{raw}]^T$ $Y_{TUBE} = M_{TUBE} X_{TUBE}$ $Y_{TUBE} = [Y_{TUBE}^{OK} \ Y_{TUBE}^{WARNING} \ Y_{TUBE}^{CRITICAL}]^T$ $X_{TUBE}$=Tube input parameter matrix: 11×1
$M_{TUBE}$=Tube Linear classifier matrix: 3×11
$Y_{TUBE}$=Tube health matrix: 3×1

The data analytics platform 110 may be configured to predict the current health of the CT overall image quality. The data analytics platform 110 includes, Matrix $X_{CT\_IQ}$ is projected onto matrix $M_{CT\_IQ}$, which is derived from training data as described in the linear classifier matrix M $Y_{CT\_IQ}$ is calculated health for cold head is classified as "OK" or "WARNING" or "CRITICAL" depending on which ever element is higher in matrix $Y_{CT\_IQ}$ $$X_{CT\_IQ}=[x_{CTW}^{raw}\ X_{CTW}^{d}\ x_{CTA}^{raw}\ x_{CTA}^{d}]^T$$

$$Y_{CT\_IQ}=M_{CT\_IQ}X_{CT\_IQ}$$

$$Y_{CT\_IQ}=[Y_{CT\_IQ}^{OK}\ Y_{CT\_IQ}^{WARNING}\ Y_{CT\_IQ}^{CRITICAL}]^T$$

$X_{CT\_IQ}$=CT IQ input parameter matrix: 4×1
$M_{CT\_IQ}$=CT IQ Linear classifier matrix: 3×4
$Y_{CT\_IQ}$=CT IQ health matrix: 3×1

Figure 5:
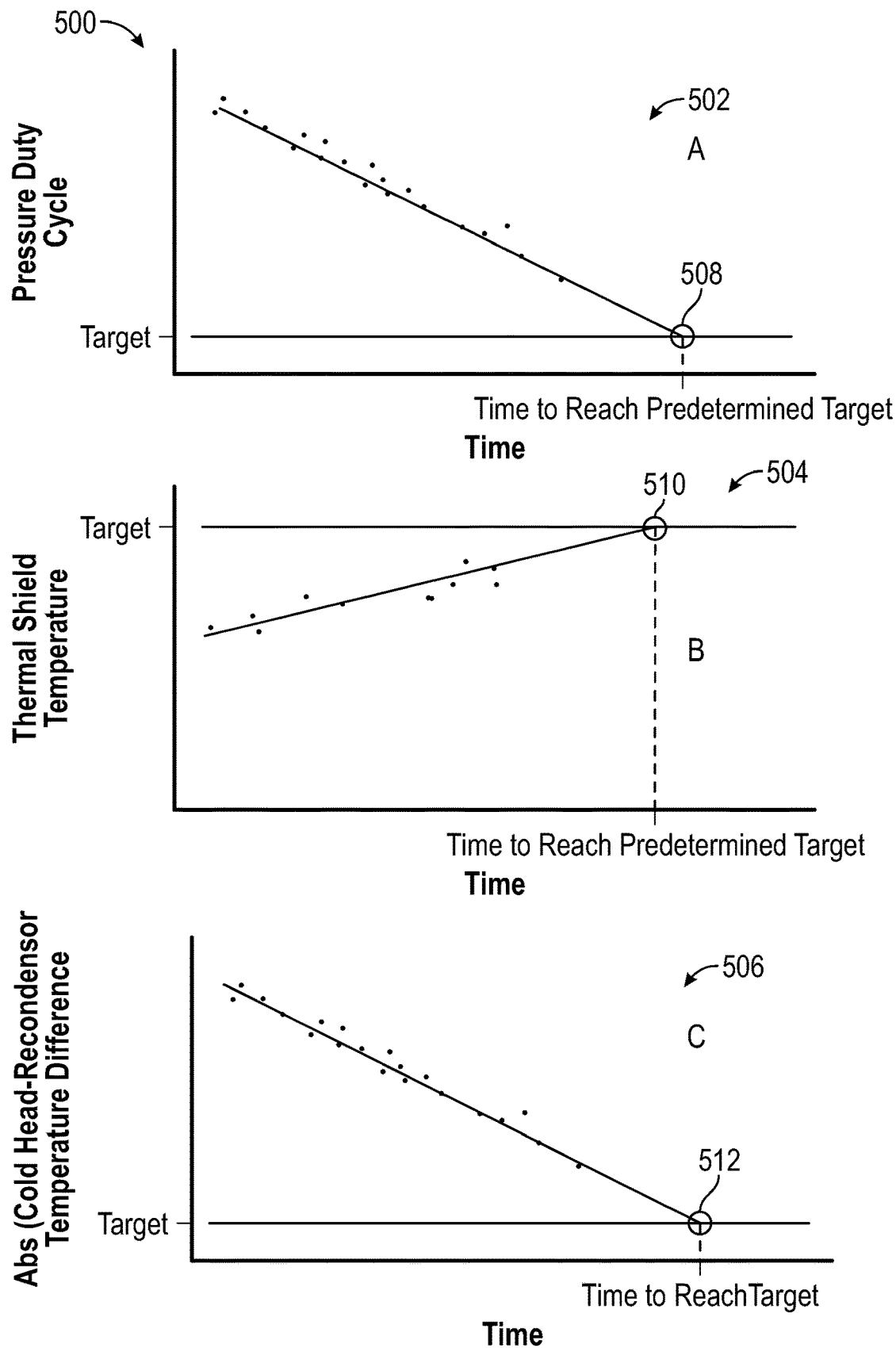
FIG. 5 is a diagram depicting the graphical representation cold head component, in accordance with one or more exemplary embodiments.

Referring to FIG. 5, FIG. 5 is a diagram 500 depicting the graphical representation cold head component, in accordance with one or more exemplary embodiments. The data analytics platform 110 may include a non-linear regression model to predict times to reach predetermined target values for the duty cycle, shield temperature and difference temperatures. The diagram 500 may depict a relation between pressure duty cycle and time graph 502, a relation between thermal shield temperature and time graph 504, and a relation between difference temperatures and time graph 506. The relation between pressure duty cycle and time graph 502 may represent various pressure levels and different time. As the pressure varies with reference to the time, then a predetermined target 508 may be reached. As the thermal shield temperature varies with reference to the time, then the predetermined target 510 may be reached. As the difference temperatures varies with reference to the time, then the predetermined target 512 may be reached. The data analytics platform 110 may be configured to report the predicted times in an order (e.g., descending order) to the end-user device 106 with prediction confidence intervals.

Figure 6:
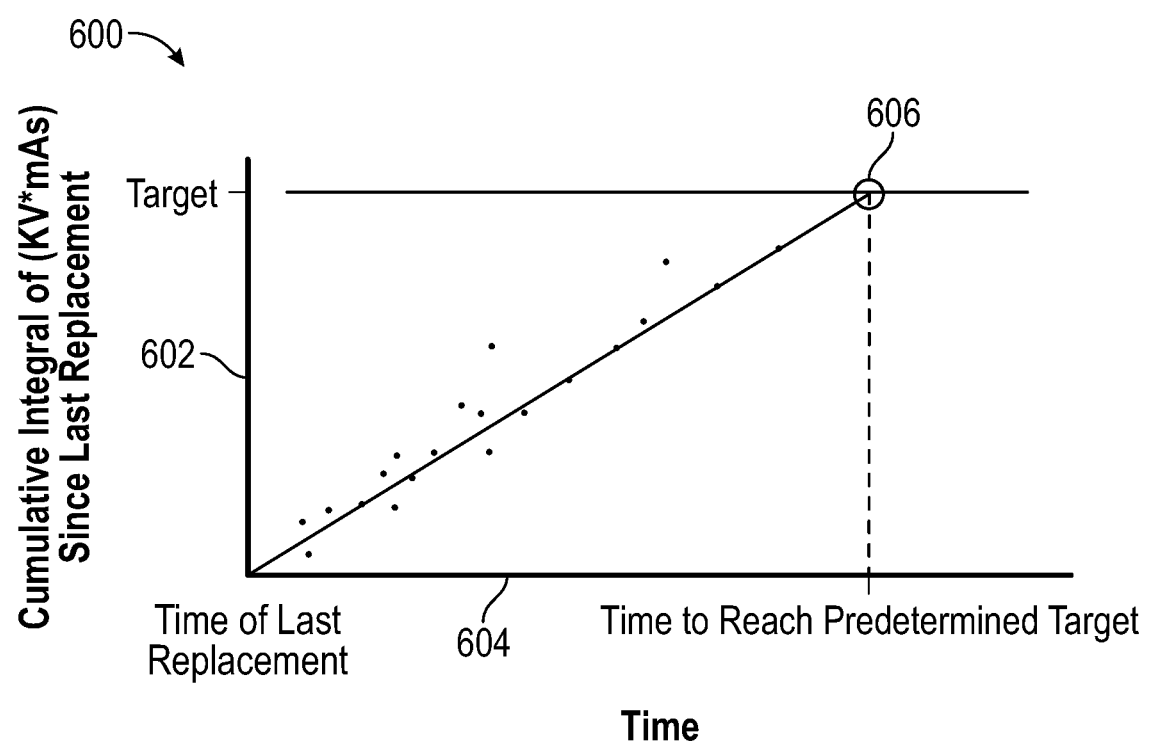
FIG. 6 is a diagram depicting the graphical representation of CT tube, in accordance one or more embodiments.

Referring to FIG. 6, FIG. 6 is a diagram 600 depicting the graphical representation of CT tube, in accordance one or more embodiments. The diagram 600 may depict the relation between the cumulative integral kv·mAs 602 and the time 604. The data analytics platform 110 may predict the time 604 to reach the predetermined target value 606 for the cumulative integral kv*mAs value 602 using the non-linear regression. The data analytics platform 110 may be configured to report the predicted values to the end-user device 106 with confidence intervals.

Figure 7:
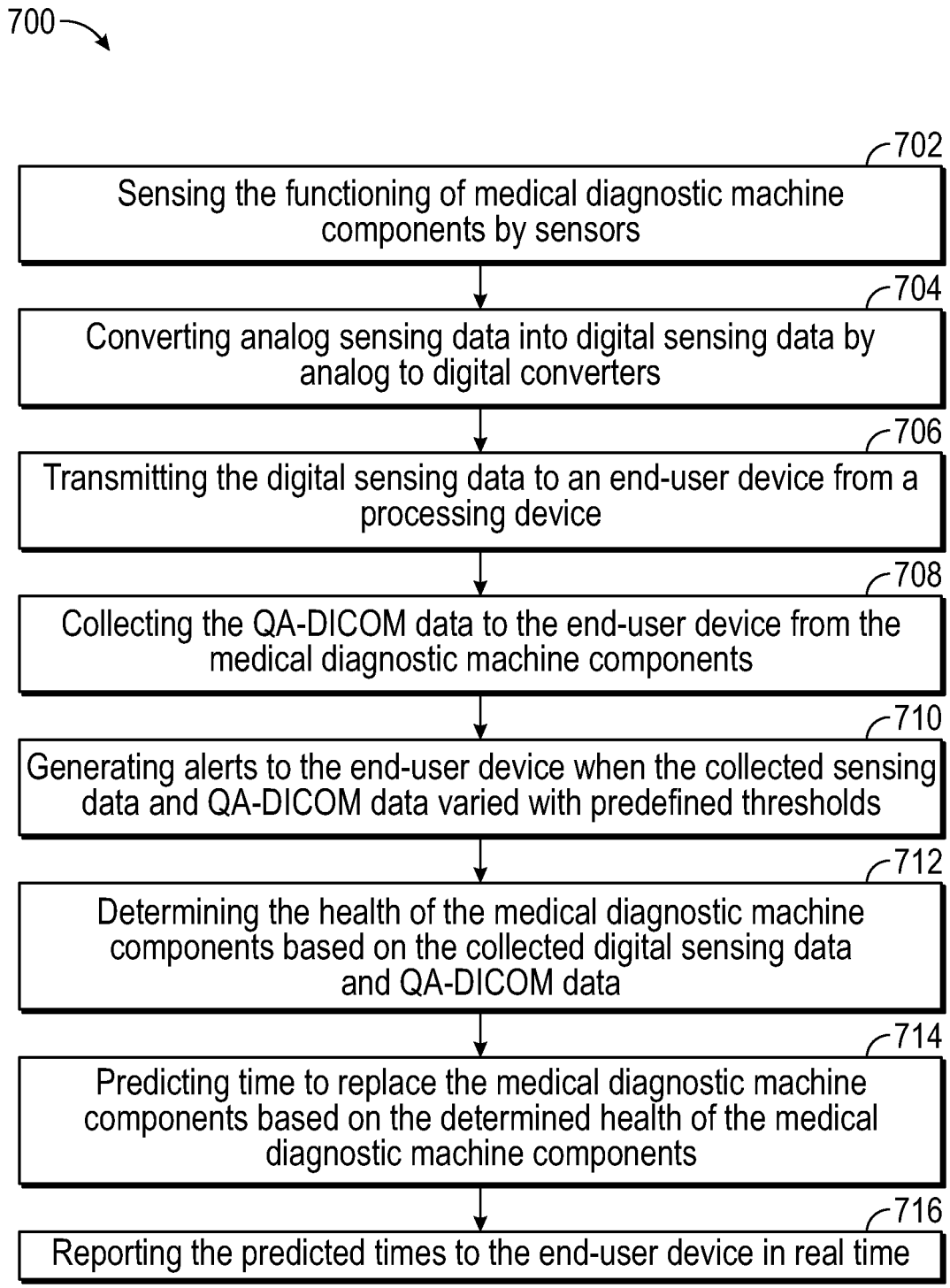
FIG. 7 is a flow diagram depicting a method of predicting the maintenance of medical diagnostic machine components.

Referring to FIG. 7, FIG. 7 is a flow diagram 700 depicting a method of predicting the maintenance of medical diagnostic machine components. According to exemplary embodiments of the present disclosure. As an option, the method 700 may be carried out in the context of the details of FIG. 1, FIG. 2, FIG. 3, and FIG. 4A-FIG. 4B, FIG. 5, and FIG. 6. However, the method 700 may also be carried out in any desired environment. Further, the aforementioned definitions may equally apply to the description below.

The method commences at step 702, where sense the functioning of medical diagnostic machine components by the sensors. An output data generated by the sensors having the analog sensing data. Convert the analog sensing data into digital sensing data by the analog to digital converters as represented by step 704. Transmit the digital sensing data to the end-user device from the processing device as represented by step 706. Collect the QA-DICOM data to end-user device from the medical diagnostic machine components as represented by step 708. Generate alerts to the end-user device when the collected sensing data and QA-DICOM data varied with predefined thresholds as represented by step 710. Determine the health of the medical diagnostic machine components based on the collected digital sensing data and QA-DICOM data as represented by step 712. Predict time to replace the medical diagnostic machine components based on the determined health of the medical diagnostic machine components as represented by step 714. Report the predicted time to the end-user device in real time as represented by step 716.

Figure 8:
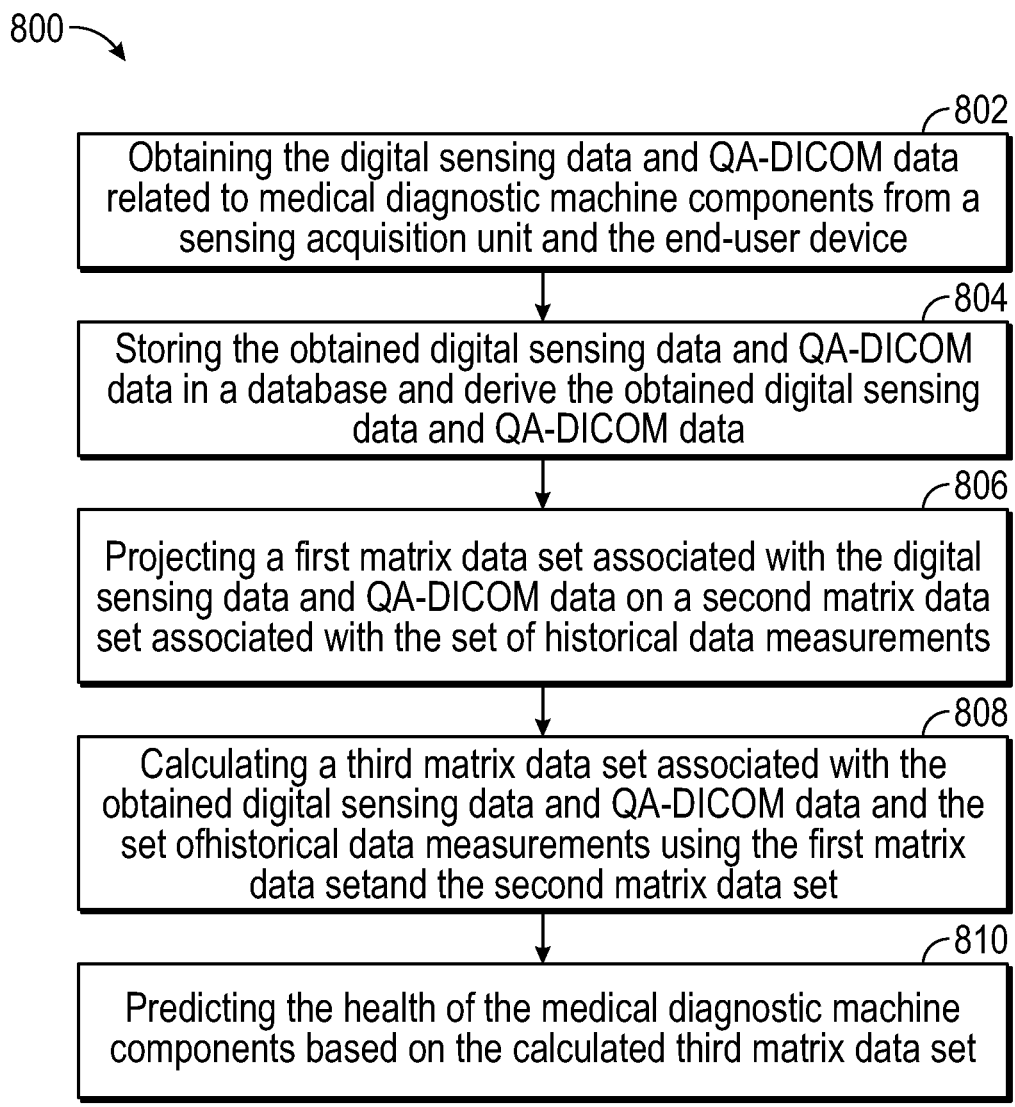
FIG. 8 is a flow diagram depicting a method of using specific matrix variables to predict the health of medical diagnostic components.

Referring to FIG. 8, FIG. 8 is a flow diagram 800 depicting a method of using specific matrix variables to predict the health of medical diagnostic components. According to exemplary embodiments of the present disclosure. As an option, the method 800 may be carried out in the context of the details of FIG. 1, FIG. 2, FIG. 3, FIG. 4, and FIG. 5, FIG. 6, and FIG. 7. However, the method 800 may also be carried out in any desired environment. Further, the aforementioned definitions may equally apply to the description below.

The method commences at step 802 where obtain digital sensing data and QA-DICOM data related to medical diagnostic machine components from the sensing acquisition unit and the end-user device. Store the obtained digital sensing data and QA-DICOM data in the database and derive the obtained digital sensing data and QA-DICOM data as represented by step 804. Project the first matrix data set associated with the digital sensing data and QA-DICOM data on the second matrix data set associated with the set of historical data measurements as represented by step 806. Calculate the third matrix data set associated with the obtained digital sensing data and QA-DICOM data and the set of historical data measurements using the first matrix data set and the second matrix data set as represented by step 808. Predict the health of the medical diagnostic machine components based on the calculated third matrix data set as represented by step 810.

More illustrative information will now be set forth regarding various optional architectures and uses in which the foregoing method may or may not be implemented, as per the desires of the user. It should be strongly noted that the following information is set forth for illustrative purposes and should not be construed as limiting in any manner. Any of the following features may be optionally incorporated with or without the exclusion of other features described.

Figure 9:
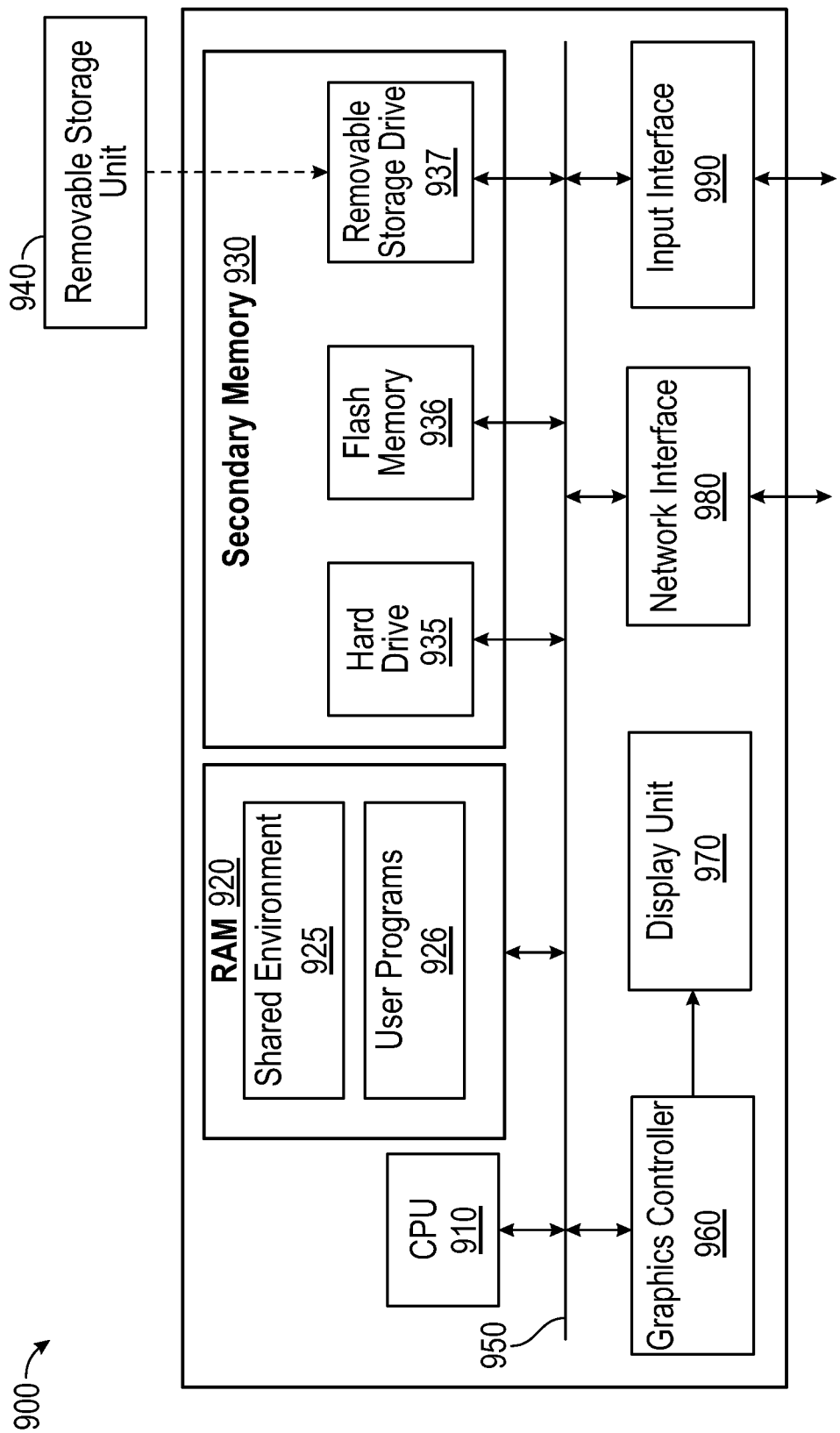
FIG. 9 is a block diagram illustrating the details of digital processing system in which various aspects of the present disclosure are operative by execution of appropriate software instructions.

Referring to FIG. 9, FIG. 9 is a block diagram illustrating the details of digital processing system 900 in which various aspects of the present disclosure are operative by execution of appropriate software instructions. Digital processing system 900 may correspond to the end-user device 106 (or any other system in which the various features disclosed above can be implemented).

Digital processing system 900 may contain one or more processors such as a central processing unit (CPU) 910, random access memory (RAM) 920, secondary memory 927, graphics controller 960, display unit 970, network interface 980, an input interface 990. All the components except display unit 970 may communicate with each other over communication path 950, which may contain several buses as is well known in the relevant arts. The components of FIG. 9 are described below in further detail.

CPU 910 may execute instructions stored in RAM 920 to provide several features of the present disclosure. CPU 910 may contain multiple processing units, with each processing unit potentially being designed for a specific task. Alternatively, CPU 910 may contain only a single general-purpose processing unit.

RAM 920 may receive instructions from secondary memory 930 using communication path 950. RAM 920 is shown currently containing software instructions, such as those used in threads and stacks, constituting shared environment 925 and/or user programs 926. Shared environment 925 includes operating systems, device drivers, virtual machines, etc., which provide a (common) run time environment for execution of user programs 926.

Graphics controller 960 generates display signals (e.g., in RGB format) to display unit 970 based on data/instructions received from CPU 910. Display unit 970 contains a display screen to display the images defined by the display signals. Input interface 990 may correspond to a keyboard and a pointing device (e.g., touch-pad, mouse) and may be used to provide inputs. Network interface 980 provides connectivity to a network (e.g., using Internet Protocol), and may be used to communicate with other systems (such as those shown in FIG. 1, network 106) connected to the network.

Secondary memory 930 may contain hard drive 935, flash memory 936, and removable storage drive 937. Secondary memory 930 may store the data software instructions (e.g., for performing the actions noted above with respect to the Figures), which enable digital processing system 900 to provide several features in accordance with the present disclosure.

Some or all of the data and instructions may be provided on the removable storage unit 940, and the data and instructions may be read and provided by removable storage drive 937 to CPU 910. Floppy drive, magnetic tape drive, CD-ROM drive, DVD Drive, Flash memory, a removable memory chip (PCMCIA Card, EEPROM) are examples of such removable storage drive 937.

The removable storage unit 940 may be implemented using medium and storage format compatible with removable storage drive 937 such that removable storage drive 937 can read the data and instructions. Thus, removable storage unit 940 includes a computer readable (storage) medium having stored therein computer software and/or data. However, the computer (or machine, in general) readable medium can be in other forms (e.g., non-removable, random access, etc.).

In this document, the term "computer program product" is used to generally refer to the removable storage unit 940 or hard disk installed in hard drive 935. These computer program products are means for providing software to digital processing system 900. CPU 910 may retrieve the software instructions, and execute the instructions to provide various features of the present disclosure described above.

The term "storage media/medium" as used herein refers to any non-transitory media that store data and/or instructions that cause a machine to operate in a specific fashion. Such storage media may comprise non-volatile media and/or volatile media. Non-volatile media includes, for example, optical disks, magnetic disks, or solid-state drives, such as storage memory 930. Volatile media includes dynamic memory, such as RAM 920. Common forms of storage media include, for example, a floppy disk, a flexible disk, hard disk, solid-state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge.

Storage media is distinct from but may be used in conjunction with transmission media. Transmission media participates in transferring information between storage media. For example, transmission media includes coaxial cables, copper wire and fiber optics, including the wires that comprise bus 950. Transmission media can also take the form of acoustic or light waves, such as those generated during radio-wave and infra-red data communications.

In some embodiments, the present disclosure provides a system for predictive maintenance of medical diagnostic machine components, the system comprising: at least one sensing information acquisition unit comprising at least one processing device, whereby the at least one processing device electrically coupled to a plurality of sensors and the plurality of sensors configured to detect functioning of medical diagnostic machine components; at least one end-user device configured to receive quality control (QA) data in digital imaging and communications in medicine (DI-COM) format from the medical diagnostic machine, and at least one data analytics platform configured to collect the sensing data and QA-DICOM data, the at least one data analytics platform configured to determine the health of the medical diagnostic machine components and predict time to replace the medical diagnostic machine components by the collected digital sensing data and QA-DICOM data using specific matrix variables, wherein the at least one data analytics platform determines the health of the medical diagnostic machine components using at least specific matrix variables and linear classifiers which are trained using singular value decomposition (SVD) based regularization techniques. In some embodiments, the system further comprises analog to digital converters electrically coupled to the at least one processing device and the analog to digital converters are configured to convert the detected analog sensing data into digital sensing data. In some embodiments, the at least one processing device configured to transmit the digital sensing data to the at least one end-user device through a network. In some embodiments, the at least one data analytics platform comprises at least one data acquisition module configured to acquire digital sensing data and QA-DICOM data from the at least one end-user device. In some embodiments, the at least one data analytics platform comprises at least one database configured to store the raw data of digital sensing data and QA-DICOM data. In some embodiments, the at least one data analytics platform further comprises at least one data deriving module configured to derive the raw data of digital sensing data and QA-DICOM data in at least one database. In some embodiments, the at least one data analytics platform further comprises at least one alert generation module configured to generate alerts to the at least one end-user device when the collected digital sensing data and QA-DICOM data varied with predefined thresholds. In some embodiments, the at least one data analytics platform further comprises at least one health component prediction module configured to predict the health of the medical diagnostic machine components based on the derived data and the predefined thresholds using the specific matrix variables. In some embodiments, the at least one data analytics platform further comprises at least one time component prediction module configured to predict time to replace the medical diagnostic machine components based on the derived data and the predefined thresholds using the specific matrix variables. In some embodiments, the at least one data analytics platform further comprises at least one interface module configured to allow users to access variables or charts in the at least one database from the at least one end-user device through application programming interface (API) requests.

In some embodiments, the present disclosure provides a method for predictive maintenance of a medical diagnostic machine components, the method comprising: obtaining digital sensing data and QA-DICOM data related to medical diagnostic machine components from at least one sensing acquisition unit and at least one end-user device; storing the obtained digital sensing data and QA-DICOM data in a database and deriving the obtained digital sensing data and QA-DICOM data; projecting at least one first matrix data set associated with the digital sensing data and QA-DICOM data on at least one second matrix data set associated with the set of historical data measurements; calculating at least one third matrix data set associated with the obtained digital sensing data and QA-DICOM data and the set of historical data measurements using the at least one first matrix data set and the at least one second matrix data set; predicting the health of the medical diagnostic machine components based on the calculated the at least one third matrix data set; and predicting time to replace the medical diagnostic machine components using a non-linear regression model, wherein the non-linear regression model comprises at least specific matrix variables and linear classifiers which are trained using singular value decomposition (SVD) based regularization techniques. In some embodiments, the method further comprises a step of generating alerts to the at least one end-user device when the obtained digital sensing data and QA-DICOM data varied with the set of historical data measurements. In some embodiments, the method further comprises a step of reporting the predicted times of the medical diagnostic machine components to the at least one end-user device. In some embodiments, the method further comprises a step of obtaining unstable results in the at least one second matrix data set while inverting the at least one first matrix data set. In some embodiments, the method further comprises a step of obtaining stable results in the at least one second matrix data set using a regularized singular value decomposition based model. In some embodiments, the method further comprises a step of sensing the functioning of the medical diagnostic machine components using a plurality of sensors. In some embodiments, the method further comprises a step of transmitting the digital sensing data to the at least one end-user device from the at least one processing device.

In some embodiments, the present disclosure provides a computer program product comprising module code embedded in a non-transitory data storage medium, wherein execution of the module code on an end-user device causes the end-user device to: obtain digital sensing data and QA-DICOM data related to medical diagnostic machine components from at least one sensing acquisition unit and at least one end-user device; store the obtained digital sensing data and QA-DICOM data in a database and deriving the obtained digital sensing data and QA-DICOM data; project at least one first matrix data set associated with the digital sensing data and QA-DICOM data on at least one second matrix data set associated with the set of historical data measurements; calculate at least one third matrix data set associated with the obtained digital sensing data and QA-DICOM data and the set of historical data measurements using the at least one first matrix data set and the at least one second matrix data set; predict the health of the medical diagnostic machine components based on the calculated the at least one third matrix data set; and predict time to replace the medical diagnostic machine components using a non-linear regression model.

In some embodiments, the present disclosure provides a method of predicting failure of a coldhead component of an MRI machine, the method comprising: deriving a coldhead component training matrix M using robust singular value decomposition on a plurality of input variables associated with the coldhead component; obtaining digital sensing data and QA-DICOM data related to the coldhead component of the MRI machine; calculating a time remaining to target as a function of the obtained digital sensing data and QA-DICOM data and the coldhead component training matrix M, wherein the target is associated with predicted failure of the coldhead component; and classifying the coldhead component as critical if the calculated time remaining to target is at or near zero. In some embodiments, the method further comprises classifying the coldhead component as warning if the calculated time remaining to target is no more than about one week. In some embodiments, the plurality of input variables comprises helium level, helium gas pressure, cold head temperature, re-condenser temperature, thermal shield temperature, helium gas low pressure, helium gas high pressure, water low temperature, water high temperature, MRI acoustic noise, and duty cycle. In some embodiments, the method further comprises sending an alert to a user if the coldhead component is classified as warning. In some embodiments, the method further comprises sending an alert to a user if the coldhead component is classified as critical.

In some embodiments, the present disclosure provides a method of predicting development of unacceptable MRI field homogeneity of an MRI machine, the method comprising: deriving an MRI field homogeneity training matrix M using robust singular value decomposition on a plurality of input variables associated with MRI field homogeneity; obtaining digital sensing data and QA-DICOM data related to MRI field homogeneity of the MRI machine; calculating a time remaining to target as a function of the obtained digital sensing data and QA-DICOM data and the MRI field homogeneity training matrix M, wherein the target is associated with unacceptable MRI field homogeneity; and classifying the MRI field homogeneity as critical if the calculated time remaining to target is at or near zero. In some embodiments, the method further comprises classifying the MRI field homogeneity as warning if the calculated time remaining to target is no more than about one week. In some embodiments, the plurality of input variables comprises magnet center frequency, signal to noise ratio, geometric accuracy in −X direction, geometric accuracy in −Y direction, and geometric accuracy in −Z direction. In some embodiments, the method further comprises sending an alert to a user if the MRI field homogeneity is classified as warning. In some embodiments, the method further comprises sending an alert to a user if the MRI field homogeneity is classified as critical.

In some embodiments, the present disclosure provides a method of predicting development of unacceptable MRI image quality of an MRI machine, the method comprising: deriving an MRI image quality training matrix M using robust singular value decomposition on a plurality of input variables associated with MRI image quality; obtaining digital sensing data and QA-DICOM data related to MRI image quality of the MRI machine; calculating a time remaining to target as a function of the obtained digital sensing data and QA-DICOM data and the MRI image quality training matrix M, wherein the target is associated with unacceptable MRI image quality; and classifying the MRI image quality as critical if the calculated time remaining to target is at or near zero. In some embodiments, the method further comprises classifying the MRI image quality component as warning if the calculated time remaining to target is no more than about one week. In some embodiments, the plurality of input variables comprises signal to noise ratio, geometric accuracy in -X direction, geometric accuracy in -Y direction, geometric accuracy in -Z direction, magnitude stability, and phase stability. In some embodiments, the method further comprises sending an alert to a user if the MRI image quality is classified as warning. In some embodiments, the method further comprises sending an alert to a user if the MRI image quality is classified as critical.

In some embodiments, the present disclosure provides a method of predicting CT tube failure in a CT machine, the method comprising: deriving a CT tube training matrix M using robust singular value decomposition on a plurality of input variables associated with MRI image quality; obtaining digital sensing data and QA-DICOM data related to CT tube failure of the CT machine; calculating a time remaining to target as a function of the obtained digital sensing data and QA-DICOM data and the CT tube training matrix M, wherein the target is associated with CT tube failure; and classifying the CT tube component as critical if the calculated time remaining to target is at or near zero. In some embodiments, the method further comprises classifying the CT tube component as warning if the calculated time remaining to target is no more than about one week. In some embodiments, the plurality of input variables comprises X-ray tube acoustic noise, and X-ray tube vibration. In some embodiments, the method further comprises sending an alert to a user if the CT tube component is classified as warning. In some embodiments, the method further comprises sending an alert to a user if the CT tube component is classified as critical.

In some embodiments, the present disclosure provides a method of predicting development of unacceptable CT image quality of an CT machine, the method comprising: deriving an CT image quality training matrix M using robust singular value decomposition on a plurality of input variables associated with CT image quality; obtaining digital sensing data and QA-DICOM data related to CT image quality of the CT machine; calculating a time remaining to target as a function of the obtained digital sensing data and QA-DICOM data and the CT image quality training matrix M, wherein the target is associated with unacceptable CT image quality; and classifying the CT image quality as critical if the calculated time remaining to target is at or near zero. In some embodiments, the method further comprises classifying the CT image quality component as warning if the calculated time remaining to target is no more than about one week. In some embodiments, the plurality of input variables comprises water CT number, and air CT number. In some embodiments, the method further comprises sending an alert to a user if the CT image quality is classified as warning. In some embodiments, the method further comprises sending an alert to a user if the CT image quality is classified as critical.

In some embodiments, the present disclosure provides a method of predicting failure of a component of an MRI machine, the method comprising: deriving an MRI component training matrix M using robust singular value decomposition on a plurality of input variables associated with the MRI component of the MRI machine; obtaining digital sensing data and QA-DICOM data related to the MRI component of the MRI machine; calculating a time remaining to target as a function of the obtained digital sensing data and QA-DICOM data and the MRI component training matrix M, wherein the target is associated with predicted failure of the MRI component; and classifying the MRI component as critical if the calculated time remaining to target is at or near zero. In some embodiments, the method further comprises classifying the MRI component as warning if the calculated time remaining to target is no more than about one week. In some embodiments, the plurality of input variables comprises helium level, helium gas pressure, cold head temperature, re-condenser temperature, thermal shield temperature, helium gas low pressure, helium gas high pressure, water low temperature, water high temperature, MRI acoustic noise, duty cycle, magnet center frequency, signal to noise ratio, geometric accuracy in -X direction, geometric accuracy in -Y direction, geometric accuracy in -Z direction, magnitude stability, and phase stability. In some embodiments, the method further comprises sending an alert to a user if the MRI component is classified as warning. In some embodiments, the method further comprises sending an alert to a user if the MRI component is classified as critical. In some embodiments, the MRI component is selected from the list of: coldhead, chiller, compressor, helium level, shimming, and system gain.

In some embodiments, the present disclosure provides a method of predicting failure of a component of a CT machine, the method comprising: deriving a CT component training matrix M using robust singular value decomposition on a plurality of input variables associated with the CT component of the CT machine; obtaining digital sensing data and QA-DICOM data related to the CT component of the CT machine; calculating a time remaining to target as a function of the obtained digital sensing data and QA-DICOM data and the CT component training matrix M, wherein the target is associated with predicted failure of the CT component; and classifying the CT component as critical if the calculated time remaining to target is at or near zero. In some embodiments, the method further comprises classifying the CT component as warning if the calculated time remaining to target is no more than about one week. In some embodiments, the plurality of input variables comprises X-ray tube acoustic noise, X-ray tube vibration, water CT number, and air CT number. In some embodiments, the method further comprises sending an alert to a user if the CT component is classified as warning. In some embodiments, the method further comprises sending an alert to a user if the CT component is classified as critical. In some embodiments, the CT component is selected from the list of: CT tube, and CT image quality.

In some embodiments, the present disclosure provides a method of reducing downtime of an MRI or CT scanner due to component failure, the method comprising deriving a component training matrix M using robust singular value decomposition on a plurality of input variables associated with the component of the MRI or CT scanner; obtaining digital sensing data and QA-DICOM data related to the component of the MRI or CT scanner; calculating a time remaining to target as a function of the obtained digital sensing data and QA-DICOM data and the component training matrix M, wherein the target is associated with predicted failure of the component; classifying the component as critical if the calculated time remaining to target is at or near zero; and scheduling repair or replacement of the component at a time before the calculated time remaining to target is at or near zero. In some embodiments, the method further comprises classifying the component as warning if the calculated time remaining to target is no more than about one week. In some embodiments, the plurality of input variables comprises helium level, helium gas pressure, cold head temperature, re-condenser temperature, thermal shield temperature, helium gas low pressure, helium gas high pressure, water low temperature, water high temperature, MRI acoustic noise, duty cycle, magnet center frequency, signal to noise ratio, geometric accuracy in −X direction, geometric accuracy in −Y direction, geometric accuracy in −Z direction, magnitude stability, phase stability, X-ray tube acoustic noise, X-ray tube vibration, water CT number, and air CT number. In some embodiments, the method further comprises sending an alert to a user if the component is classified as warning. In some embodiments, the method further comprises sending an alert to a user if the component is classified as critical. In some embodiments, the component is selected from the list of: coldhead, chiller, compressor, helium level, shimming, system gain, and image quality.

Reference throughout this specification to "one embodiment", "an embodiment", or similar language means that a particular feature, structure, or characteristic described in connection with the embodiment is included in at least one embodiment of the present disclosure. Thus, appearances of the phrases "in one embodiment", "in an embodiment" and similar language throughout this specification may, but do not necessarily, all refer to the same embodiment.

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub combinations of the various features described herein above as well as variations and modifications thereof, which would occur to persons skilled in the art upon reading the foregoing description.

EXAMPLES

Example 1

A system for predictive maintenance of medical diagnostic machine components, the system comprising:
- at least one sensing information acquisition unit comprising at least one processing device, whereby the at least one processing device electrically coupled to a plurality of sensors and the plurality of sensors configured to detect functioning of medical diagnostic machine components;
- at least one end-user device configured to receive quality control (QA) data in digital imaging and communications in medicine (DICOM) format from the medical diagnostic machine, and
- at least one data analytics platform configured to collect the sensing data and QA-DICOM data, the at least one data analytics platform configured to determine the health of the medical diagnostic machine components and predict time to replace the medical diagnostic machine components by the collected digital sensing data and QA-DICOM data using specific matrix variables,
- wherein the at least one data analytics platform determines the health of the medical diagnostic machine components using at least specific matrix variables and linear classifiers which are trained using singular value decomposition (SVD) based regularization techniques.

Example 2

The system of Example 1, further comprising analog to digital converters electrically coupled to the at least one processing device and the analog to digital converters are configured to convert the detected analog sensing data into digital sensing data.

Example 3

The system of Example 2, wherein the at least one processing device configured to transmit the digital sensing data to the at least one end-user device through a network.

Example 4

The system of Example 1, wherein the at least one data analytics platform comprises at least one data acquisition module configured to acquire digital sensing data and QA-DICOM data from the at least one end-user device.

Example 5

The system of Example 1, wherein the at least one data analytics platform comprises at least one database configured to store the raw data of digital sensing data and QA-DICOM data.

Example 6

The system of Example 1, wherein the at least one data analytics platform further comprises at least one data deriving module configured to derive the raw data of digital sensing data and QA-DICOM data in at least one database.

Example 7

The system of Example 1, wherein the at least one data analytics platform further comprises at least one alert generation module configured to generate alerts to the at least one end-user device when the collected digital sensing data and QA-DICOM data varied with predefined thresholds.

Example 8

The system of Example 1, wherein the at least one data analytics platform further comprises at least one health component prediction module configured to predict the health of the medical diagnostic machine components based on the derived data and the predefined thresholds using the specific matrix variables.

Example 9

The system of Example 1, wherein at least data analytics platform further comprises at least one time component prediction module configured to predict time to replace the medical diagnostic machine components based on the derived data and the predefined thresholds using the specific matrix variables.

Example 10

The system of Example 1, wherein the at least one data analytics platform further comprises at least one interface module configured to allow users to access variables or charts in the at least one database from the at least one end-user device through application programming interface (API) requests.

Example 11

A method for predictive maintenance of a medical diagnostic machine components, comprising:
  obtaining digital sensing data and QA-DICOM data related to medical diagnostic machine components from at least one sensing acquisition unit and at least one end-user device;
  storing the obtained digital sensing data and QA-DICOM data in a database and deriving the obtained digital sensing data and QA-DICOM data;
  projecting at least one first matrix data set associated with the digital sensing data and QA-DICOM data on at least one second matrix data set associated with the set of historical data measurements;
  calculating at least one third matrix data set associated with the obtained digital sensing data and QA-DICOM data and the set of historical data measurements using the at least one first matrix data set and the at least one second matrix data set;
  predicting the health of the medical diagnostic machine components based on the calculated the at least one third matrix data set; and
  predicting time to replace the medical diagnostic machine components using a non-linear regression model,
  wherein the non-linear regression model comprises at least specific matrix variables and linear classifiers which are trained using singular value decomposition (SVD) based regularization techniques.

Example 12

The method of Example 11, further comprising a step of generating alerts to the at least one end-user device when the obtained digital sensing data and QA-DICOM data varied with the set of historical data measurements.

Example 13

The method of Example 11, further comprising a step of reporting the predicted times of the medical diagnostic machine components to the at least one end-user device.

Example 14

The method of Example 11, further comprising a step of obtaining unstable results in the at least one second matrix data set while inverting the at least one first matrix data set.

Example 15

The method of Example 11, further comprising a step of obtaining stable results in the at least one second matrix data set using a regularized singular value decomposition based model.

Example 16

The method of Example 11, further comprising a step of sensing the functioning of the medical diagnostic machine components using a plurality of sensors.

Example 17

The method of Example 11, further comprising a step of transmitting the digital sensing data to the at least one end-user device from the at least one processing device.

Example 18

A computer program product comprising module code embedded in a non-transitory data storage medium, wherein execution of the module code on an end-user device causes the end-user device to:
  obtain digital sensing data and QA-DICOM data related to medical diagnostic machine components from at least one sensing acquisition unit and at least one end-user device;
  store the obtained digital sensing data and QA-DICOM data in a database and deriving the obtained digital sensing data and QA-DICOM data;
  project at least one first matrix data set associated with the digital sensing data and QA-DICOM data on at least one second matrix data set associated with the set of historical data measurements;
  calculate at least one third matrix data set associated with the obtained digital sensing data and QA-DICOM data and the set of historical data measurements using the at least one first matrix data set and the at least one second matrix data set;
  predict the health of the medical diagnostic machine components based on the calculated the at least one third matrix data set; and
  predict time to replace the medical diagnostic machine components using a non-linear regression model.

Example 19

A method of predicting failure of a coldhead component of an MRI machine, the method comprising:
  deriving a coldhead component training matrix M using robust singular value decomposition on a plurality of input variables associated with the coldhead component;
  obtaining digital sensing data and QA-DICOM data related to the coldhead component of the MRI machine;
  calculating a time remaining to target as a function of the obtained digital sensing data and QA-DICOM data and the coldhead component training matrix M, wherein the target is associated with predicted failure of the coldhead component; and
  classifying the coldhead component as critical if the calculated time remaining to target is at or near zero.

Example 20

The method of Example 19, wherein the plurality of input variables comprises helium level, helium gas pressure, cold head temperature, re-condenser temperature, thermal shield temperature, helium gas low pressure, helium gas high pressure, water low temperature, water high temperature, MRI acoustic noise, and duty cycle.

Example 21

The method of Example 19 or Example 20 further comprising sending an alert to a user if the coldhead component is classified as warning.

Example 22

The method of any one of Examples 19-21 further comprising sending an alert to a user if the coldhead component is classified as critical.

Example 23

A method of predicting development of unacceptable MRI field homogeneity of an MRI machine, the method comprising:
  deriving an MRI field homogeneity training matrix M using robust singular value decomposition on a plurality of input variables associated with MRI field homogeneity;
  obtaining digital sensing data and QA-DICOM data related to MRI field homogeneity of the MRI machine;
  calculating a time remaining to target as a function of the obtained digital sensing data and QA-DICOM data and the MRI field homogeneity training matrix M, wherein the target is associated with unacceptable MRI field homogeneity; and
  classifying the MRI field homogeneity as critical if the calculated time remaining to target is at or near zero.

Example 24

The method of Example 23, wherein the plurality of input variables comprises magnet center frequency, signal to noise ratio, geometric accuracy in −X direction, geometric accuracy in −Y direction, and geometric accuracy in −Z direction.

Example 25

The method of Example 23 or Example 24 further comprising sending an alert to a user if the MRI field homogeneity is classified as warning.

Example 26

The method of any one of Examples 23-25 further comprising sending an alert to a user if the MRI field homogeneity is classified as critical.

Example 27

A method of predicting development of unacceptable MRI image quality of an MRI machine, the method comprising:
  deriving an MRI image quality training matrix M using robust singular value decomposition on a plurality of input variables associated with MRI image quality;
  obtaining digital sensing data and QA-DICOM data related to MRI image quality of the MRI machine;
  calculating a time remaining to target as a function of the obtained digital sensing data and QA-DICOM data and the MRI image quality training matrix M, wherein the target is associated with unacceptable MRI image quality; and
  classifying the MRI image quality as critical if the calculated time remaining to target is at or near zero.

Example 28

The method of Example 27, wherein the plurality of input variables comprises signal to noise ratio, geometric accuracy in −X direction, geometric accuracy in −Y direction, geometric accuracy in −Z direction, magnitude stability, and phase stability.

Example 29

The method of Example 27 or Example 28 further comprising sending an alert to a user if the MRI image quality is classified as warning.

Example 30

The method of any one of Examples 27-29 further comprising sending an alert to a user if the MRI image quality is classified as critical.

Example 31

A method of predicting CT tube failure in a CT machine, the method comprising:
  deriving a CT tube training matrix M using robust singular value decomposition on a plurality of input variables associated with MRI image quality;
  obtaining digital sensing data and QA-DICOM data related to CT tube failure of the CT machine;
  calculating a time remaining to target as a function of the obtained digital sensing data and QA-DICOM data and the CT tube training matrix M, wherein the target is associated with CT tube failure; and
  classifying the CT tube component as critical if the calculated time remaining to target is at or near zero.

Example 32

The method of Example 31, wherein the plurality of input variables comprises X-ray tube acoustic noise, and X-ray tube vibration.

Example 33

The method of Example 31 or Example 32 further comprising sending an alert to a user if the CT tube component is classified as warning.

Example 34

The method of any one of Examples 31-33 further comprising sending an alert to a user if the CT tube component is classified as critical.

Example 35

A method of predicting development of unacceptable CT image quality of an CT machine, the method comprising:
  deriving an CT image quality training matrix M using robust singular value decomposition on a plurality of input variables associated with CT image quality;
  obtaining digital sensing data and QA-DICOM data related to CT image quality of the CT machine;
  calculating a time remaining to target as a function of the obtained digital sensing data and QA-DICOM data and the CT image quality training matrix M, wherein the target is associated with unacceptable CT image quality; and
  classifying the CT image quality as critical if the calculated time remaining to target is at or near zero.

Example 36

The method of Example 35, wherein the plurality of input variables comprises water CT number, and air CT number.

Example 37

The method of Example 35 or Example 36 further comprising sending an alert to a user if the CT image quality is classified as warning.

Example 38

The method of any one of Examples 35-37 further comprising sending an alert to a user if the CT image quality is classified as critical.

Example 39

A method of predicting failure of a component of an MRI machine, the method comprising:
deriving an MRI component training matrix M using robust singular value decomposition on a plurality of input variables associated with the MRI component of the MRI machine;
obtaining digital sensing data and QA-DICOM data related to the MRI component of the MRI machine;
calculating a time remaining to target as a function of the obtained digital sensing data and QA-DICOM data and the MRI component training matrix M, wherein the target is associated with predicted failure of the MRI component; and
classifying the MRI component as critical if the calculated time remaining to target is at or near zero.

Example 40

The method of Example 39, wherein the plurality of input variables comprises helium level, helium gas pressure, cold head temperature, re-condenser temperature, thermal shield temperature, helium gas low pressure, helium gas high pressure, water low temperature, water high temperature, MRI acoustic noise, duty cycle, magnet center frequency, signal to noise ratio, geometric accuracy in -X direction, geometric accuracy in -Y direction, geometric accuracy in -Z direction, magnitude stability, and phase stability.

Example 41

The method of Example 39 or Example 40 further comprising sending an alert to a user if the MRI component is classified as warning.

Example 42

The method of any one of Examples 39-41 further comprising sending an alert to a user if the MRI component is classified as critical.

Example 43

The method of any one of Examples 39-42, wherein the MRI component is selected from the list of: coldhead, chiller, compressor, helium level, shimming, and system gain.

Example 44

A method of predicting failure of a component of a CT machine, the method comprising:
deriving a CT component training matrix M using robust singular value decomposition on a plurality of input variables associated with the CT component of the CT machine;
obtaining digital sensing data and QA-DICOM data related to the CT component of the CT machine;
calculating a time remaining to target as a function of the obtained digital sensing data and QA-DICOM data and the CT component training matrix M, wherein the target is associated with predicted failure of the CT component; and
classifying the CT component as critical if the calculated time remaining to target is at or near zero.

Example 45

The method of Example 44, wherein the plurality of input variables comprises X-ray tube acoustic noise, X-ray tube vibration, water CT number, and air CT number.

Example 46

The method of Example 44 or Example 45 further comprising sending an alert to a user if the CT component is classified as warning.

Example 47

The method of any one of Examples 44-46 further comprising sending an alert to a user if the CT component is classified as critical.

Example 48

The method of any one of Examples 44-47, wherein the CT component is selected from the list of: CT tube, and CT image quality.

Example 49

A method of reducing downtime of an MRI or CT scanner due to component failure, the method comprising:
deriving a component training matrix M using robust singular value decomposition on a plurality of input variables associated with the component of the MRI or CT scanner;
obtaining digital sensing data and QA-DICOM data related to the component of the MRI or CT scanner;
calculating a time remaining to target as a function of the obtained digital sensing data and QA-DICOM data and the component training matrix M, wherein the target is associated with predicted failure of the component;
classifying the component as critical if the calculated time remaining to target is at or near zero; and
classifying the component as warning if the calculated time remaining to target is no more than about one week.

Example 50

The method of Example 49, wherein the plurality of input variables comprises helium level, helium gas pressure, cold head temperature, re-condenser temperature, thermal shield temperature, helium gas low pressure, helium gas high pressure, water low temperature, water high temperature, MRI acoustic noise, duty cycle, magnet center frequency, signal to noise ratio, geometric accuracy in -X direction, geometric accuracy in −Y direction, geometric accuracy in −Z direction, magnitude stability, phase stability, X-ray tube acoustic noise, X-ray tube vibration, water CT number, and air CT number.

Example 51

The method of Example 49 or Example 50 further comprising sending an alert to a user if the component is classified as warning.

Example 52

The method of any one of Examples 49-51 further comprising sending an alert to a user if the component is classified as critical.

Example 53

The method of any one of Examples 49-52, wherein the component is selected from the list of: coldhead, chiller, compressor, helium level, shimming, system gain, and image quality.

What is claimed is:

1. A method of reducing downtime of an MRI or CT scanner due to component or image quality failure, the method comprising:
    deriving training matrices using robust singular value decomposition or matrix inversion techniques on a plurality of input variables associated with various components of MRI or CT machines and image quality parameters;
    obtaining digital sensing data and QA-DICOM data from the MRI or CT scanner;
    projecting the obtained digital sensing data and QA-DICOM data onto the training matrices to provide a health matrix of the various components;
    comparing elements in the health matrix to predefined threshold values associated with each of the elements;
    classifying the performance of the components or the image quality into following categories: "normal", "warning" or "critical" based at least on the compared elements; and
    calculating a time remaining to take a service action as a function of the obtained digital sensing data, QA-DICOM data and the training matrix, wherein the time remaining to take a service action is associated with predicted failure of the component or image quality.

2. The method of claim 1, wherein the plurality of input variables comprises helium level, helium gas pressure, cold head temperature, re-condenser temperature, thermal shield temperature, helium gas low pressure, helium gas high pressure, water low temperature, water high temperature, MRI acoustic noise, duty cycle, magnet center frequency, signal to noise ratio, geometric accuracy in −X direction, geometric accuracy in −Y direction, geometric accuracy in −Z direction, magnitude stability, and phase stability.

3. The method of claim 1 further comprising sending an alert to a user if the component or image quality is classified as warning or critical, wherein the alert enables the user to access analysis results using API calls.

4. The method of claim 1, wherein:
    the MRI or CT scanner is an MRI scanner;
    the component or image quality failure is coldhead failure; and
    the step of deriving training matrices using robust singular value decomposition or matrix inversion techniques on a plurality of input variables associated with various components of MRI or CT machines and image quality parameters comprises deriving a coldhead training matrix using robust singular value decomposition or matrix inversion techniques on a plurality of input variables associated with the coldhead of the MRI.

5. The method of claim 4, wherein the plurality of input variables comprises helium level, helium gas pressure, cold head temperature, re-condenser temperature, thermal shield temperature, helium gas low pressure, helium gas high pressure, water low temperature, water high temperature.

6. The method of claim 4 further comprising sending an alert to a user if the coldhead performance is classified as warning or critical, wherein the alert enables the user to access analysis results using API calls.

7. The method of claim 1, wherein:
    the MRI or CT scanner is a CT scanner;
    the component or image quality failure is CT tube failure; and
    the step of deriving training matrices using robust singular value decomposition or matrix inversion techniques on a plurality of input variables associated with various components of MRI or CT machines and image quality parameters comprises deriving a component training matrix using robust singular value decomposition or matrix inversion techniques on a plurality of input variables associated with the tube of the CT.

8. The method of claim 7, wherein the plurality of input variables comprises X-ray tube acoustic noise and X-ray tube vibration.

9. The method of claim 7 further comprising sending an alert to a user if the CT tube performance is classified as warning or critical, wherein the alert enables the user to access analysis results using API calls.

10. The method of claim 1, wherein:
    the MRI or CT scanner is an MRI scanner;
    the component or image quality failure is unacceptable MRI field homogeneity; and
    the step of deriving training matrices using robust singular value decomposition or matrix inversion techniques on a plurality of input variables associated with various components of MRI or CT machines and image quality parameters comprises deriving an MRI field homogeneity training matrix using robust singular value decomposition or matrix inversion techniques on a plurality of input variables associated with MRI field homogeneity.

11. The method of claim 10, wherein the plurality of input variables comprises magnet center frequency, signal to noise ratio, geometric accuracy in −X direction, geometric accuracy in −Y direction, and geometric accuracy in −Z direction.

12. The method of claim 10 further comprising sending an alert to a user if the MRI field homogeneity performance is classified as warning or critical, wherein the alert enables the user to access analysis results using API calls.

13. The method of claim 1, wherein:
    the MRI or CT scanner is an MRI scanner;
    the component or image quality failure is MRI image quality failure; and
    the step of deriving training matrices using robust singular value decomposition or matrix inversion techniques on a plurality of input variables associated with various components of MRI or CT machines and image quality parameters comprises deriving an MRI image quality training matrix using robust singular value decomposition or matrix inversion techniques on a plurality of input variables associated with MRI image quality.

14. The method of claim 13, wherein the plurality of input variables comprises signal to noise ratio, geometric accuracy in –X direction, geometric accuracy in –Y direction, geometric accuracy in –Z direction, magnitude stability, and phase stability.

15. The method of claim 13 further comprising sending an alert to a user if the MRI image quality is classified as warning or critical, wherein the alert enables the user to access analysis results using API calls.

16. The method of claim 1, wherein:
the MRI or CT scanner is a CT scanner;
the component or image quality failure is CT image quality failure; and
the step of deriving training matrices using robust singular value decomposition or matrix inversion techniques on a plurality of input variables associated with various components of MRI or CT machines and image quality parameters comprises deriving an CT image quality training matrix using robust singular value decomposition or matrix inversion techniques on a plurality of input variables associated with CT image quality.

17. The method of claim 16, wherein the plurality of input variables comprises water CT number, and air CT number.

18. The method of claim 16 further comprising sending an alert to a user if the CT image quality is classified as warning or critical, wherein the alert enables the user to access analysis results using API calls.

19. The method of claim 1, wherein the plurality of input variables comprises X-ray tube acoustic noise, X-ray tube vibration, water CT number, and air CT number.

* * * * *